United States Patent [19]

Wilson

[11] 4,196,730
[45] Apr. 8, 1980

[54] LIQUID DRUG DISPENSER

[76] Inventor: Dennis R. Wilson, 39 Sugar Leaf Ct., St. Charles, Mo. 63301

[21] Appl. No.: 820,697

[22] Filed: Aug. 1, 1977

[51] Int. Cl.² .......................... A61M 5/00; A61M 5/00
[52] U.S. Cl. ....................... 128/214; 128/218 A; 128/DIG. 12; 222/142; 222/144; 222/145
[58] Field of Search ........... 128/214 F, 218 R, 218 A, 128/218 F, 218 C, 273, 215, DIG. 12, 234, 236, 173 H; 222/135, 144, 144.5, 142, 145

[56] References Cited

U.S. PATENT DOCUMENTS

| | | | |
|---|---|---|---|
| 2,531,267 | 11/1950 | Narnisch | 128/218 F |
| 2,627,270 | 2/1953 | Glass | 128/218 A |
| 2,671,448 | 3/1954 | Narnisch | 128/218 F |
| 2,879,767 | 3/1959 | Kulick | 128/227 |
| 3,714,943 | 2/1973 | Yanof et al. | 128/215 X |
| 3,858,581 | 1/1975 | Kamen | 128/218 A |
| 3,880,138 | 4/1975 | Wootten et al. | 128/218 A X |
| 3,985,133 | 12/1976 | Jenkins et al. | 128/214 F |
| 4,006,736 | 2/1977 | Kranys et al. | 128/2 A |

*Primary Examiner*—Dalton L. Truluck
*Attorney, Agent, or Firm*—Rogers, Eilers & Howell

[57] ABSTRACT

A liquid dispenser has a transparent frame which houses a rotatable mounting assembly of a plurality of mounted liquid compressible containers having needle discharge outlets having covering caps to block liquid flow. A control unit can be operated so that the mounting assembly is rotated by a motor secured to the frame, and locked in position by a solenoid powered lock pin mounted to the frame which engages the mounting assembly. When the mounting assembly is locked into discharge position, a selected container needle is aligned with a discharge passage in the frame. Then a motor-driven compression drive unit secured to the frame is operated to move a gear rack forward so that a flange secured to the rack engages the end of the liquid container to drive it forward to cause the container needle to puncture its cover cap and also a diaphragm at the frame discharge passage. After the diaphragm is punctured, the flange compresses the liquid in the container through the container needle through the frame discharge passage. A three-way valve is connected to the frame discharge passage to connect the passage to a catheter extending to a needle inserted in the body of a patient. Another catheter connects the valve to a bag of dextrose. A wheel is mounted to the frame with a link engaged to a handle operating the valve so that a drive ramp attached to the rack rotates the wheel to move the valve handle simultaneously with forward rack movement to allow discharge of the liquid from the frame passage through the catheter extending to the patient. A scale associated with the frame and with the compression drive unit indicates to the operator how much liquid has been discharged through the needle extending into the patient's body. The rack can be driven rearward so that the wheel can move the valve handle to position the valve to connect the dextrose bag with the needle in the patient.

48 Claims, 9 Drawing Figures

LIQUID DRUG DISPENSER

BACKGROUND OF THE INVENTION

This invention pertains to automatic dispensing of liquid drug from containers, and is more particularly related to mounting of liquid containers so that a certain container can be selected and placed in a discharge position for discharge of its contained drug through an outlet to a patient. This invention pertains to dispensation of drugs in intensive care rooms, emergency rooms, and other emergency areas by paramedic teams and the like.

In the prior art there has been great need of a fast and simple way of dispensing a selected drug to a patient in need of the drug, especially in emergency situations. Such a need arises in intensive care units and in emergency rooms of hospitals, as well as at emergency sites arising on the job, such as a construction work site, or in an office building, when a patient has suffered a catastrophe such as a heart attack. When such an emergency situation arises, it is very important to dispense the necessary drug to the patient as fast as possible, and each second of delay after the emergency can be crucial. For example, in the case of a heart attack, the brain begins to suffer damage shortly after the heart stops beating and within two minutes serious damage can occur. Complete destruction of the brain can occur within six minutes. Therefore, dispensation of a life-saving drug, such as epinephrine, as quickly as possible, can be of great benefit to the patient.

In the prior art there has been a lack of a device that can deliver a selected drug from a plurality of drugs, and dispense that drug to a patient with speed, effectiveness, and a minimum of manual effort. Generally, a principal method of copying with an emergency situation in which a patient is in need of a drug is to perform a number of manual steps concerned with removal of sterile covers from tubes and bags and the like, connecting tubing, waiting for the development of fluid flow to certain points, and insertion of a syringe needle into a catheter tube leading to the patient. Repetition of these steps is necessary for each drug that is to be dispensed. This manual method generally requires two or more people and can be time-consuming and cumbersome with a requirement for great dexterity on the part of the participants. The emergency team must also carry the emergency components to an emergency site and the lack of a pre-existing arrangement of components causes delay and difficulty in transporting the emergency equipment.

In the prior art there are devices which have compression members that engage the plungers of syringes held in fixed position for dispensing drug from the syringe. There are also prior art devices which control the distance of travel of a member used to drive the syringe such as by the use of a number of spacers to adjust the distance travelled.

SUMMARY OF THE INVENTION

The present invention overcomes the problems in the prior art. The invention comprises a transparent plexiglass frame which houses a rotatable mounting assembly having a plurality of drug syringes or other like drug containers, which are capable of being compressed to discharge fluid contained within the plungers through discharge needles. The syringes are spring mounted so as to be biased rearwardly in the mounting assembly with room for their forward movement within the mounting assembly when the spring bias is overcome. The number of containers and their size can be selected according to the need for the quantity and variety of drugs necessary for the dispenser, with adjustment in size of the frame allowing for a greater or smaller number of containers within it.

A control unit operates a motor to rotate the mounted syringes so that a selected syringe can be positioned in alignment with a frame discharge passage. To accomplish this, the mounting assembly has a lock disc secured to it which has bores designed to receive a pin projected from a solenoid operated by the control unit. Thus the operator of the control unit can activate the solenoid pin to lock the disc and mounting assembly in position for syringe discharge.

The syringe needles have caps covering their ends which prevent fluid leaking from them during their positioning in the container until discharge time. When a selected syringe is positioned for discharge, a motor driven compression flange secured to a gear rack mounted to the frame is moved forward to engage the plunger. As the flange is driven forward, it overcomes the spring bias, and urges the syringe body forward due to the internal compressive resistance forces contained within the syringe due to the blocking by the needle cap. The syringe needle is moved forward until its cap engages a diaphragm at the frame discharge passage so that by such engagement the needle cap and diaphragm are punctured, to allow compression of fluid from the syringe into the discharge passage.

Another feature of the invention is that the discharge conduit opening is controlled by a positioning assembly comprising a three-way valve, which can be a stop cock valve. The stop cock valve has one flow line in fluid connection with the discharge passage and another flow line connected to a catheter which extends to a needle inserted in the patient. The third stop cock line is connected to a bag of dextrose. The stop cock can be initially operated to fill the discharge passage and catheter extending to the patient with dextrose. A linkage arrangement operates the stop cock valve by virtue of the movement of a ramp mounted on the compressive rack. A wheel mounted to the frame is rotated by forward ramp movement to drive a link to move the stop cock. By the time the discharge passage diaphragm is punctured, the valve line is open to establish flow from the discharge passage through the needle inserted into the patient's body.

A measuring scale inscribed on the frame is used in conjunction with a measuring stem secured to the compressive rack to read the amount of fluid discharged into the patient's body. This scale is calibrated so that a positive reading for the amount of drug discharged into the patient does not begin until the volume of fluid discharged from the selected syringe has filled the tubing from the discharge passage to the needle inserted in the body.

Upon complete discharge, the fluid in the container of the compression flange engages the syringe mounting assembly and the resistance to the flange movement is transferred to the motor driving it to operate an automatic switch to reverse the direction of the rack movement. As the rack moves rearward, its ramp again drives the wheel to operate the stop cock to block flow through the outlet passage; as the rack flange moves rearwardly, the syringe spring urges the syringe needle away from the diaphragm. After the flange has been moved to a rearward position, the mounting assembly can again be rotated to align another selected drug container with the discharge passage and compression of the drug through the discharge passage is performed without removing the needle from the patient's body and without having to manually remove the first discharged syringe.

Thus any number of selected drugs can be dispensed from a plurality of containers without having to remove the needle from the patient's body, and without manual operation of the syringes or of valves. A convenient means of reading the amount of drug discharged into the patient is provided. The invention thus allows a single operator of the control unit to select a needle drug and dispense it to the patient with a minimum of manual effort and with precision. The transparent frame allows the operator to examine the mounting assembly components should for any reason a malfunction arise, and a hinged lid on top of the frame allows for access to components within the frame. The invention thus provides features long needed in the medical field and of great need to those suffering in an emergency situation.

The invention can be utilized in intensive care units, emergency rooms, by paramedic teams, and in other emergency locations, as well as utilized for dispensation of drugs in non-emergency situations.

DESCRIPTION OF THE PREFERRED EMBODIMENT

Figure 1:
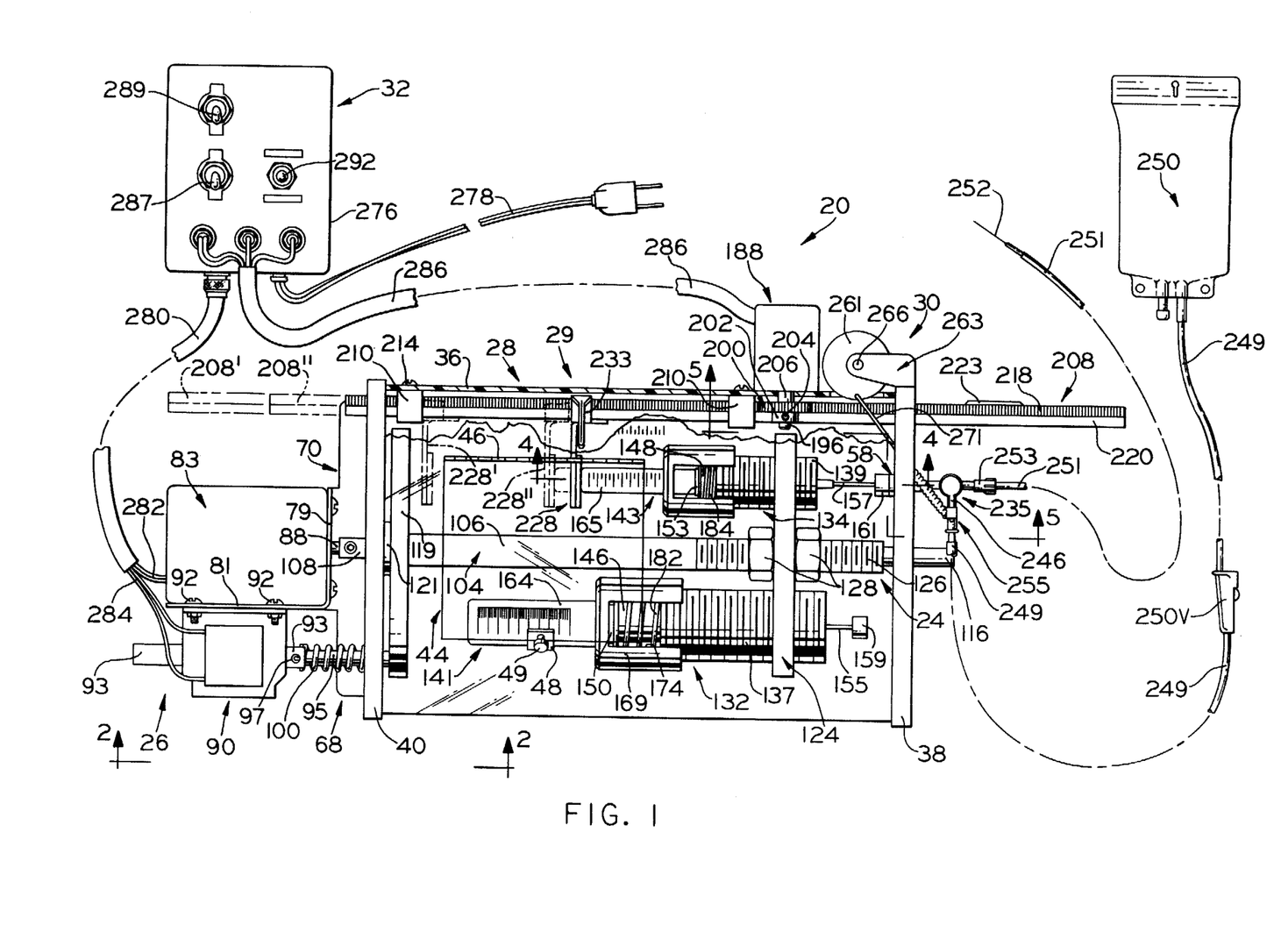
FIG. 1 is a top plan view of the dispenser showing the control unit detached from the frame; part of the frame cylinder is broken to better show components and phantom lines are used to show various positions of the gear rack and the small syringe plunger.

The liquid drug dispenser 20 has its rear and front ends respectively shown as the left and right ends of FIG. 1. Dispenser 20 comprises a frame 22 which houses a rotatable drug mounting assembly 24 that is rotated and positioned by a power and positioning assembly 26 secured to the left end of the frame 22. The dispenser 20 further comprises a compression drive assembly 28, shown secured to the frame at the top of FIG. 1, a measuring assembly 29, and a stop cock positioning assembly 30 shown at the top front end of FIG. 1. These dispenser components are controlled by a control unit 32.

Frame 22 comprises a transparent cylindrical midsection 36 which has its front and rear ends secured within conforming circular recesses in transparent front and rear upright end plates 38 and 40 respectively, as by an adhesive such as epoxy glue. The bottom surfaces of end plates 38 and 40 are flat to provide stable support for the frame.

Figure 3:
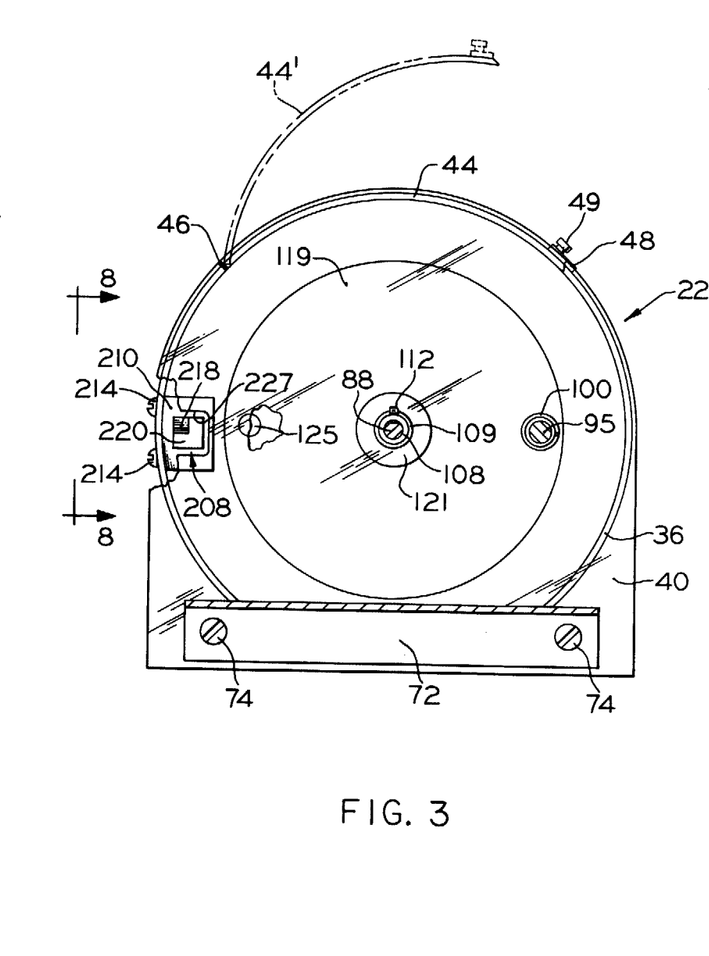
FIG. 3 is a rear end view of the dispenser taken on line 3—3 of FIG. 2, showing part of the left side frame broken and showing the frame lid in open position in phantom lines.

At the top rear of the cylindrical 36 is a transparent lid 44 of arcuate cross section conforming to that of cylinder 36, and hinged at 46 to the cylinder so that the lid 44 fits snugly within a conforming opening in the top of the cylinder 36 and can pivot upward as shown in phantom lines in FIG. 3 to permit access to the components within the cylinder. Lid 44 can be held shut against the cylinder by a fastener 48 which has a handle 49. Cylinder 36, lid 44, and end plates 38 and 40, can all be made of a transparent rigid plastic such as plexiglass.

Figure 4:
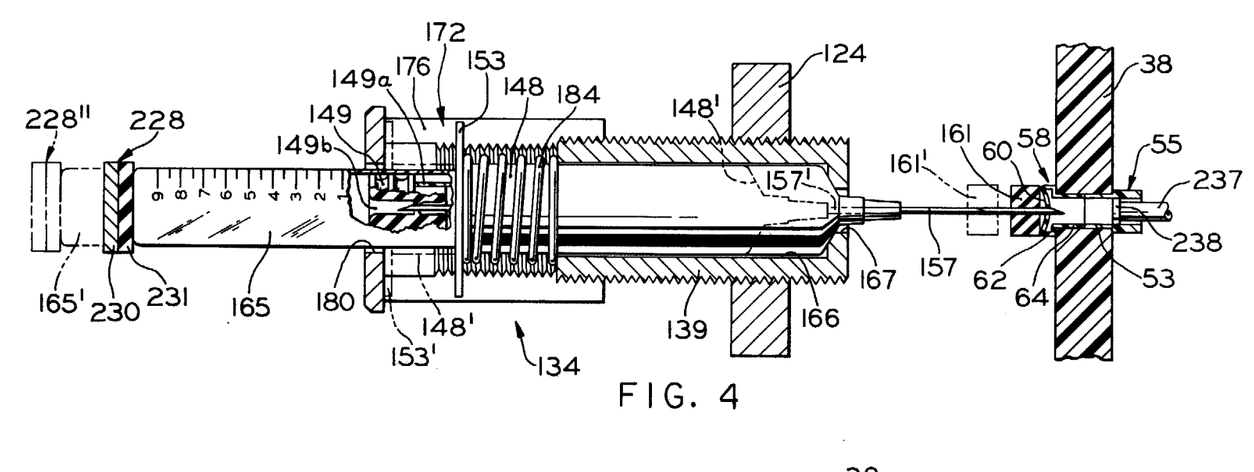
FIG. 4 is a side sectional view taken on the line 4—4 of FIG. 1 of the smaller syringe container and part of the mounting assembly showing certain parts in phantom lines.

Front end plate 38 has a cylindrical outlet bore, as seen specifically in FIG. 4, which receives the smaller conforming end 53 of an outlet tube 55. A puncture tube 58 has a flexible diaphragm 60 extending across the end of an inner cylindrical section 62 which extends frontwardly into a smaller cylindrical tubular section 64 that fits within the outlet bore with its end abutting the end of outlet tube section 53. Liquid is injected through the diaphragm 60 into the puncture tube 58 and outlet tube 55 as will be described. Outlet tube 55 is preferably made of a rigid plastic material, as are the sections 62 and 64 of the diaphragm tube 58, while the diaphragm 60 is preferably made of a flexible material such as rubber which is molded to section 62 of the diaphragm tube. The diaphragm 60 is shown in a flexed puncture position in FIG. 4, but when not flexed it assumes a vertical position.

The power and positioning assembly 26 located at the rear of the dispenser comprises a unitary metal mounting bracket 68 having subsections including a lower angle shape portion 70 extending across the bottom of end plate 40 with the lower vertical flange 72 of the angle portion being secured flush against the end plate 40 by screws 74. Bracket 68 extends from the upper horizontal flange of angle 70 upwardly into a vertical section 79. A rearwardly extending section 81 extends from the upper edge of section 79, so that an L-shaped bracket section, as seen in FIG. 1, is formed to mount a motor and solenoid to be described.

An AC motor 83 is mounted by screws 86 to bracket section 79 so that the motor shaft 88 extends through a bore in section 79 to permit the shaft 88 to engage the shaft of the rotatable drug mounting assembly as will be described.

Figure 2:
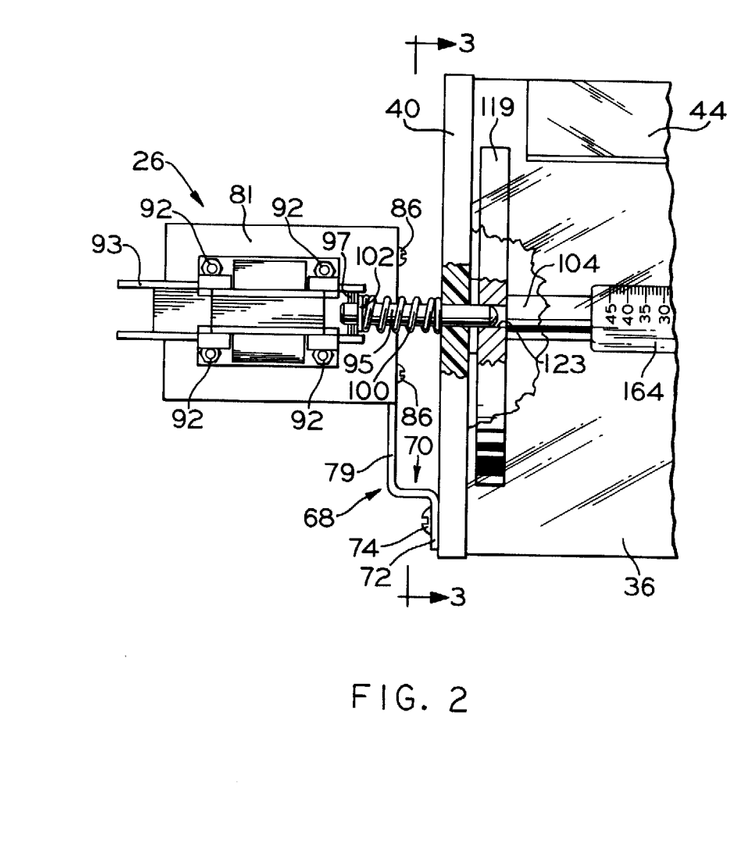
FIG. 2 is a side plan view of the rear end of the dispenser, taken on line 2—2 of FIG. 1, with parts of the frame and locking disc broken and shown in section, and with the plunger rod shown in a locked position.

A solenoid 90 is mounted by screws 92 to bracket section 81 (FIGS. 1 and 2). Solenoid 90 has its core engaged to a pair of metal plates 93, and a metal lock rod 95 having its rear end secured by a vertical pin 97 to plates 93 extends telescopically through a conforming bore to the side of rear end plate 40 (FIGS. 2 and 3), and a coil spring 100 is positioned between end plate 40 and a flat washer 102 surrounding rod 95 adjacent pin 97 so that the rod 95 is biased outward away from end plate 40 into a disengaging position from the rotatable drug mounting assembly, as will be described.

The assembly 26 acts to power and hold in position the drug mounting assembly 24 so that the compression drive assembly 28 can act in cooperation with mounting assembly 24 to dispense the selected drug. Mounting assembly 24 comprises a unitary cylindrical shaft 104 having a large midsection 106 axially center positioned within cylinder 36. Midsection 106 extends rearwardly into a smaller cylindrical end section 108, which extends through a centrally located bore in rear end plate 40, with a cylindrical bushing 109, which can be of brass, secured within the bore as by epoxy glue. The bushing 109 fits around section 108 to act as a bearing to guide axial rotation. Rear shaft section 108 has a bore extending inwardly from its end to receive a chordal shaped key section of motor shaft 88. A set screw 112 extends through section 108 to engage the key of motor shaft 88 to permit driving engagement of motor shaft 88 with mount shaft 104 as seen in FIGS. 1 and 3.

Mount shaft midsection 106 extends forwardly into a smaller cylindrical section 116 which is snugly received by and extends through a conforming cylindrical metal bushing secured by adhesive within a centrally located cylindrical bore in front end plate 38 so that the bushing acts as a rotational bearing. The snug fit to shaft end sections 108 and 116 within their conforming bushings which are axially aligned in the end plate bores allows for smooth axial rotation of shaft 104. At the rear of shaft 104, section 108 extends through a circular disc lock plate 119, which can be made of metal and is fixedly secured to shaft 104 as by a set screw (not shown) so that disc 119 rotates integrally with shaft 104. To reduce rotational friction, disc 119 is spaced from rear end plate 40 by a spacer washer 121 surrounding the shaft section 108. Disc 119 has two cylindrical bores 123 and 125 diametrically spaced and both of slightly larger diameter than lock rod 95 so that they may telescopically receive rod 95 to thereby hold the disc 119 and shaft 104 in fixed position relative to the frame, the rod 95 being shown so inserted in FIG. 2.

The mount assembly 24 further comprises an elongated wing plate 124, which can be of metal, having a central internally threaded bore to threadingly engage the threaded front end 126 of shaft midsection 106. A pair of jam nuts 128 positioned on both sides of wing plate 124 hold it in fixed position on shaft 104. Secured at the ends of wing 124 are syringe assemblies 132 and 134, which have the same basic shape, but differ in size. Assemblies 132 and 134 (refer to FIG. 4 for detailed showing of assembly 134) have externally threaded sleeves 137 and 139 respectively which screw into threaded bores at the ends of wing 124 so that they are held in fixed position relative to the wing. The sleeves 137 and 139 each support syringes 141 and 143 respectively. These are standard syringes, syringe 143 being shown specifically in FIG. 4. Syringes 141 and 143 each have tubular bodies 146 and 148, respectively, which can be of transparent durable plastic with respective flanges 150 and 153 extending integrally at the rear ends of the bodies, and needles 155 and 157 extending at the front of the bodies partially into rubber cylindrical puncture caps 159 and 161 which block fluid flow through the needle outlets. Cylindrical plunger tubes 164 and 165 which can be of rigid durable transparent plastic extend into syringe bodies 146 and 148, respectively, around sealing rubber washers mounted as by a screw fit on concentric mounting cylinders within the bodies which are secured to the frame interior end of the bodies. The washer and mounting cylinder for syringe 143 are shown as 148, and 149a, respectively, with the washer orifice shown as 149b. The needles 157 and 159 extend rearwardly from the front of the syringes through centrally located orifices in the washers so that as the plungers are moved inwardly around the washers through the bodies, the liquid in the plunger is compressed through the washer orifice and through the needles. Syringe 143 is shown in the extended position with phantom lines. The plungers 164 and 165 are each marked with parallel numbered lines as seen in the drawings, so that when the plungers are moved from their extended positions, the number of milliliters of drug dispensed can be determined by looking at the position of the numbered plunger lines relative to the rear end of the syringe washers. This type of measurement is well known in the art. Syringe 143 has a liquid capacity of ten milliliters when its plunger is in the extended position, and can be filled with a liquid drug as an epinephrine. Syringe 141 has a liquid capacity of fifty milliliters when its plunger is extended, and can be filled with a liquid drug such as calcium chloride.

Sleeves 137 and 139 each have bores conforming in shape to the syringe bodies 146 and 148, the bore 166 for sleeve 139 being shown in FIG. 4, as well as a counterbore extending through the front of the sleeve, shown as counterbore 167 in FIG. 4, to allow extension of the needle and front part of the body through the sleeve front. The syringe bodies are thus telescopically received by the sleeve bores, so that their axes are parallel to the shaft 104 axis.

The syringe assemblies 132 and 134 each have cylindrically shaped internally threaded metal caps 169 and 172, each having a pair of diametrically opposed slots 174 and 176 in their cylindrical walls respectively. The caps can screw onto the rear ends of the threaded sleeves 137 and 139 with the syringe flanges 150 and 153 extended through the cap slots 174 and 176. The rear walls of caps 169 and 172 each have bores large enough to permit rearward extension of the plungers, but small enough to resist rearward movement of the flanges, one such bore 180 being shown in FIG. 4. Caps 169 and 172 are threaded onto their sleeves so that when the front of the syringe bodies engage the front of the sleeve bores, the washers are positioned with their rear ends just forward of the rear ends of the caps, as shown for washer 149 and cap 172 in FIG. 4. Coil springs 182 and 184 are respectively positioned between the syringe flanges 150 and 153 and the rear ends of the sleeves 137 and 139, thus biasing the flanges rearwardly away from the sleeves and against the rear walls of the slots. In the phantom lines of FIG. 4 the syringe flanges in the extended position are shown as 153', so that the syringe body and needle have the positions shown as 148' and 157'. The components of syringe 141 assume similar positions when in the extended position shown in FIG. 1.

Each of the syringe assemblies 132 and 134 are positioned on wing 124 so that the needles 155 and 157 can each be rotated into axial alignment with the puncture tube 58 by rotation of shaft 104. The bores 123 and 125 are positioned in disc 119 so that engagement of solenoid lock pin 95 in bore 123 locks needle 157 into axial alignment with tube 48, while engagement in disc bore 125 locks needle 155 into axial alignment with tube 58.

Figure 5:
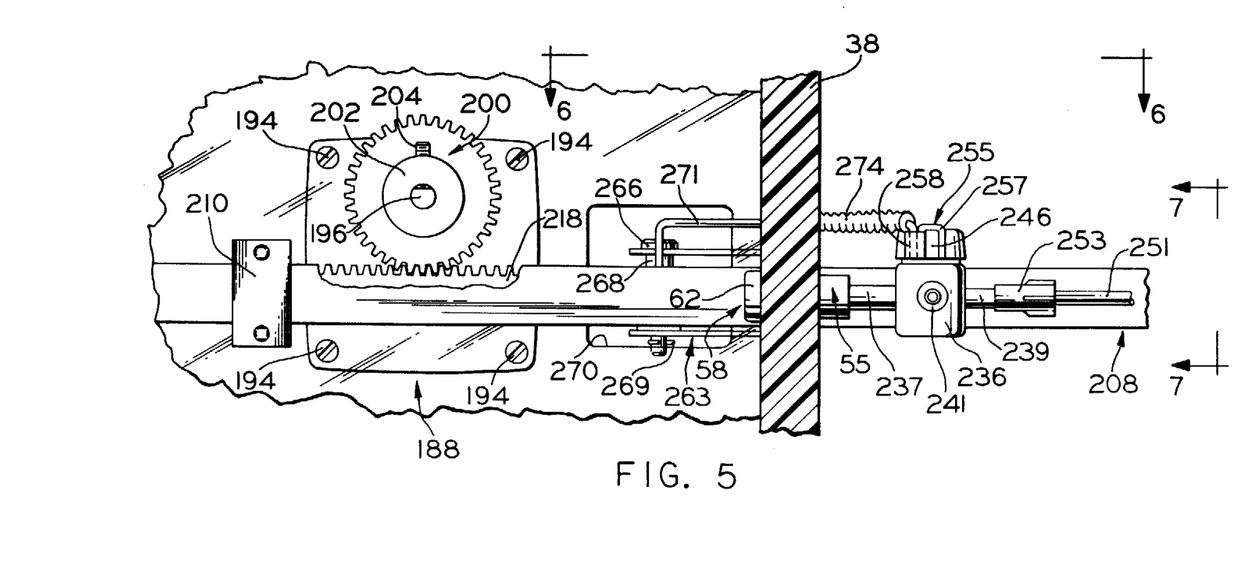
FIG. 5 is a side section view of the front part of the dispenser taken on the line 5—5 of FIG. 1 showing the stop cock and its linkage arrangement and with part of the gear rack being shown broken.

The compression drive assembly 28 acts to drive the syringes forward and drive the plungers to compress the fluid within the syringes when the selected syringe needle is brought into alignment with puncture tube 58. The drive assembly 28 comprises a reversible drive AC motor 188 having its housing 190 securely mounted to the side of cylinder 36 by screws 194. The motor 188 has a shaft 196 having a flat keyed surface upon which is mounted a cylindrical gear 200. Motor 188 is a commercially available motor, such as Hurst Manufacturing Corporation's (Princeton, Indiana) 7 watt, 6 RPM, 115 volts, Model T that has an internal switch that reverses the rotation of shaft 196 from counterclockwise rotation (as viewed in FIG. 5) to clockwise rotation when shaft 196 is met by a predetermined amount of resistance to counterclockwise rotation. Gear 200 has a cylindrical inner hub 202 through which a set screw 204 extends to directly engage the gear to the shaft flat, and an outer hub 206 which telescopically extends through a circular bore in the side of cylinder 36, so that rotation of shaft 196 drivingly rotates gear 200.

The compression drive assembly 28 further comprises a linear rectangular shaped gear rack 208 which telescopically extends through conforming square bores in a pair of mounting brackets 210, which can be of metal, and which are firmly secured to the side wall of cylinder 36 as by screws 214. The bores of brackets 210 are in horizontal alignment with their axes parallel with the axes of shaft 104 and which allows the rack 208 to move through the brackets 210 in a path parallel with shaft 104.

Figure 6:
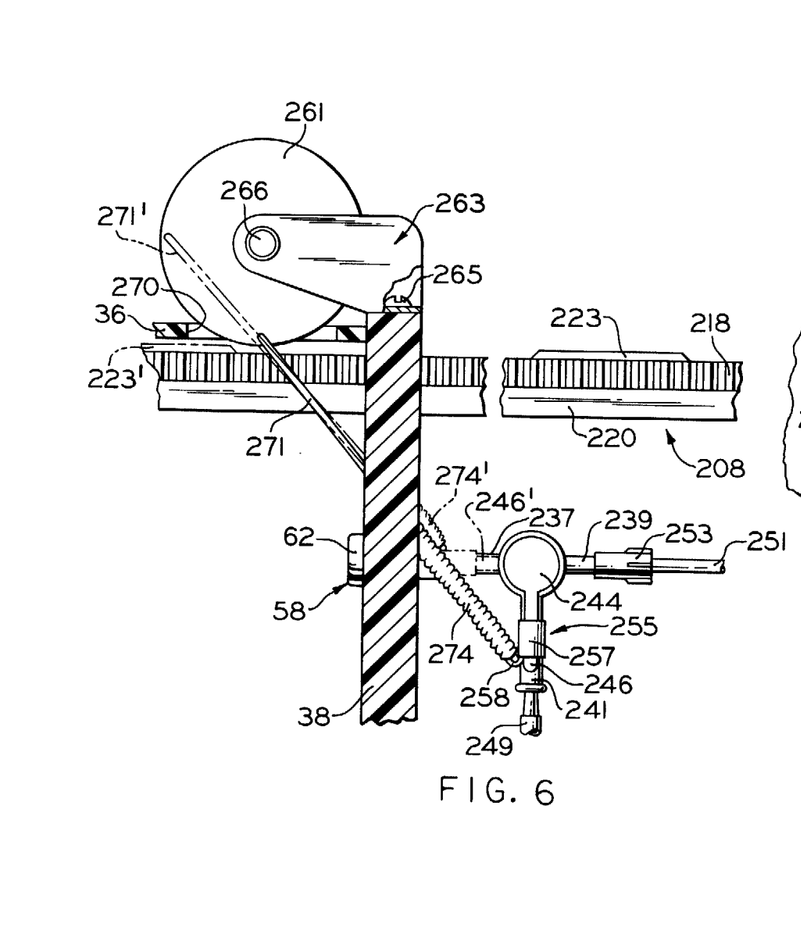
FIG. 6 is a top sectional view taken on the line 6—6 of FIG. 5 of the front end of the dispenser showing some parts in phantom lines.
Figure 7:
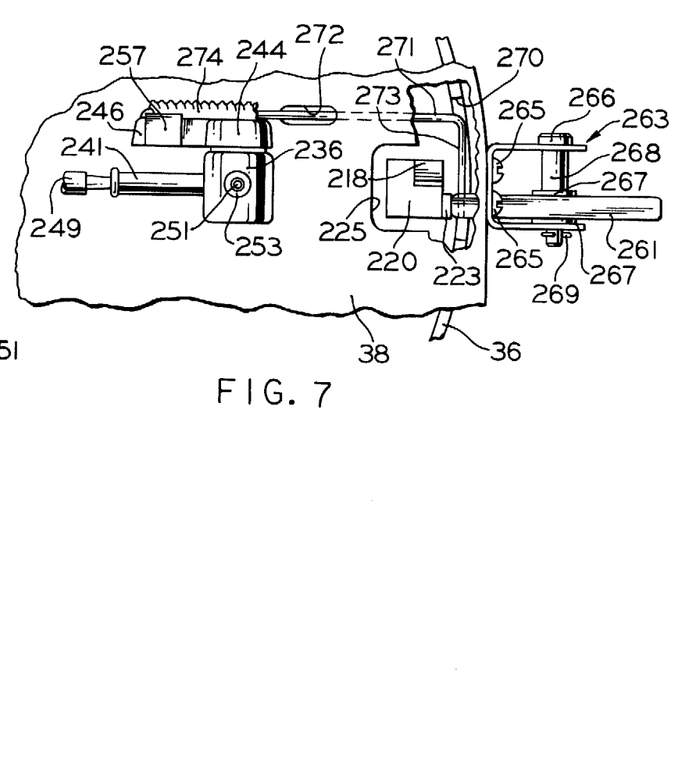
FIG. 7 is a front end view of part of the dispenser taken on the line 7—7 of FIG. 5 showing part of the frame broken.

Gear rack 208 comprises a linear gear teeth section 218 of general rectangular shape which can be brass, and which extends along the upper outer corner of the rack and is firmly secured as by screws (not shown) to a mounting section 220 of the rack 208, which can be of metal such as steel. The cross section of the rack sections 220 is such that when section 218 is mounted upon section 220, the rack 208 has a square cross section, as seen in FIGS. 3 and 7. Secured to the outer side of rack 208, as by screws (not shown) is a wheel drive ramp 223, which can be of metal, and is slanted at each of its ends inward towards rack 208 as seen in FIG. 6, to permit smooth engagement with a wheel of the stop cock positioning assembly to be described.

Rack 208 extends through generally square-shaped bores 225 and 227 in end plates 38 and 40. The bores 225 and 227 are in horizontal alignment with each other and with the bores of mounting brackets 210, thus permitting rack 208 to move horizontally through each of the end plates without interference. The teeth 218 of rack 208 are in mesh with gear 200 so that rotation of the gear 200 by motor shaft 196 causes horizontal movement of the rack 208 through its mounting brackets 210.

An L-shaped drive flange 228, which can be of metal, has one of its rectangular flange legs 229 firmly secured flush against the inside of rack section 220 as by screws (not shown). The other flange leg 230 extends perpendicular to rack 208, and a resilient pad 231, which can be of rubber, is secured to the front of leg 230, as by glue, to provide smoothness of engagement against the ends of the plungers. Leg 230 has a length such that it extends far enough inward to drivingly engage the rear end of each of the syringe plungers, such engagement being shown against plunger 165 in FIGS. 1 and 4.

When rack 208 is in its rearmost position, shown as 208' in FIG. 1, the flange 228 is in the position shown as 228' with its rearward movement blocked by engagement against the rearmost bracket 210. In this position the syringe plungers when in their rearmost positions, can be rotated by shaft 104 without jarring against the flange leg 230.

Figure 8:
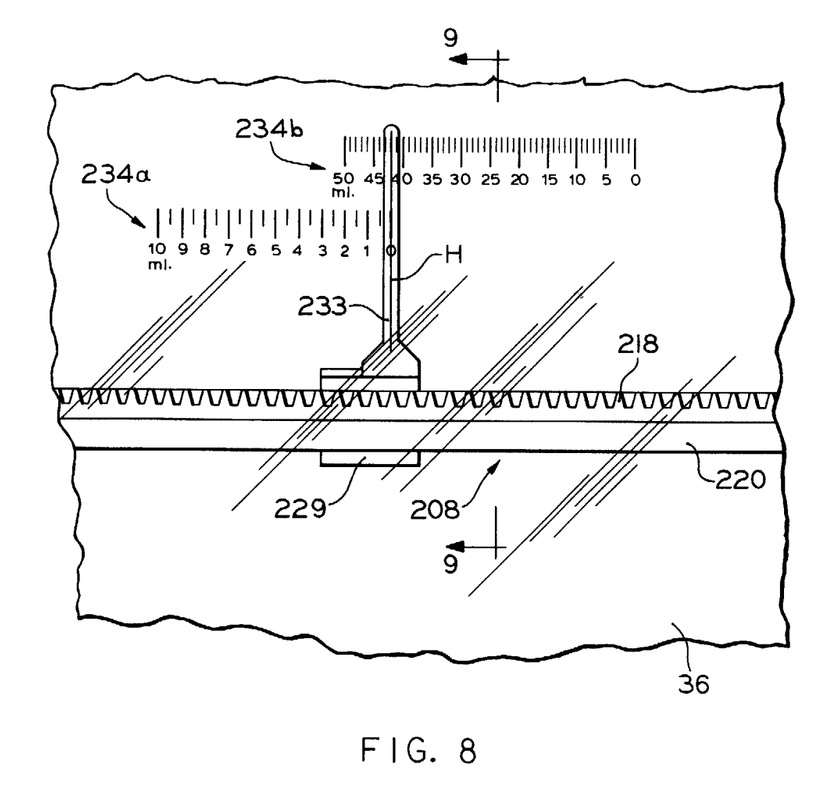
FIG. 8 is a top plan view of part of the frame showing the measuring assembly.
Figure 9:
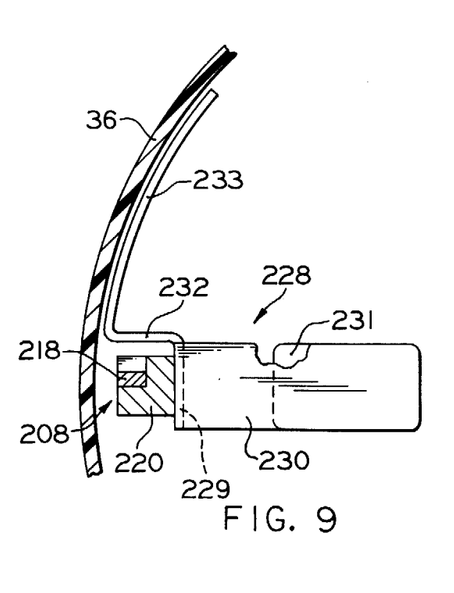
FIG. 9 is a section taken on the line 9—9 of FIG. 8 showing part of the measuring assembly and compression drive unit.

Measuring assembly 29 is comprised of two calibrated scales and an extension from flange 228 A measuring extension has a horizontal plate 232 extending integrally outwardly from the top of flange leg 229, with a curved measuring stem 233 extending upwardly from the exterior end of plate 232, as seen in FIG. 9, with a straight measuring hairline H inscribed on the exterior side of stem 233, as seen in FIG. 8. Measuring assembly 29 further comprises two measuring scales 234a and 234b. Scale 234a has numbered parallel milliliter measuring lines that are inscribed on the interior of cylinder 36 and spaced apart the same distance as the numbered milliliter discharge lines on plunger 165, and are used to indicate the amount of drug discharged into the patient through a needle yet to be described. Stem hairline H is aligned with the scale 234a line for zero milliliters discharged when flange 228 is positioned against the end of plunger 165 when the plunger numbered lines indicate three milliliters have been discharged from plunger 165, as will be later illustrated. The three milliliter discharge lag results because of the volume of tubes between the needle 157 and a needle to be described. As the rack 208 moves forward from this position, stem 233 moves forward with it such that the number of milliliters shown on the scale 234a numbered lines aligned with hairline H equals the volume of epinephrine discharged into the patient at that point. This allows the operator to discharge a measured amount of the epinephrine in the syringe by viewing the measuring assembly 29. Likewise, scale 234b has numbered milliliters lines that correspond to the volume lines on plunger 164, so that the scale line for zero milliliters discharged is aligned with hairline H when flange 228 is against the end of plunger 164 with three milliliters discharged from plunger 164, and the numbered lines on plunger 264 indicate a remaining plunger volume of forty-seven milliliters. This allows the operator to visibly measure the amount of calcium chloride discharge through an insertion needle in the patient.

The stop cock positioning assembly 30 is driven by rack 208 as will be described. Stop cock assembly 30 comprises a stop cock valve 235, which is a standard stop cock with a lower barrel 236 having extending into it an integral inlet tube 237 with a circular flange 238 at its end that is telescopically snugly received (FIG. 4) within tube 55 so that end 238 seals against the inner wall of tube 55. An adhesive sealant can be used on end 238 to assist the sealing. An integral discharge tube 239 extends from barrel 236 on the opposite side of tube 237. A third integral tube 241 extends into barrel 235 perpendicular to tubes 237 and 239.

Barrel 236 is open at its upper end and receives within it a valve section 244 having an integral upper handle 246 extending outwardly therefrom. Stop cock 235 has the structure for valve 244 well known in the art that provides for liquid flow to be established between tubes 237 and tube 239, when handle 246 is in the position shown in solid lines in FIG. 6, with tube 241 being closed from communication with tubes 237 and 239 in that position. With the handle in the position shown in phantom lines as 246' in FIG. 6, tube 241 is in liquid communication with tube 239, with tube 237 being blocked from liquid communication with those tubes. All parts of stop cock 235 can be made of rigid plastic.

A flexible plastic catheter tube 249 is inserted snugly within the end of tube 241 and extends into liquid communication to a bag 250 filled with a liquid solution of dextrose, and positioned above the stop cock so that gravity flow of the dextrose to the stop cock can be maintained. Catheter 249 has a hand operable crimp valve 250v operable to crimp tube 249, to block dextrose flow from the bag. Stop cock tube 239 is in liquid communication with a flexible plastic catheter 251 by engagement of a sleeve coupling 253 which can be of plastic. A needle 252 is engaged to the end of catheter 251 for discharge of fluid.

Stop cock handle 246 has a linkage clip 255 which can be metal and which has a springy "u" shaped clamp section 257 which clamps firmly around the handle 246. A rolled cylindrical tab 258 extends integrally from the end of clamp 257 to receive the end of a link rod to be described.

The stop cock assembly further comprises a wheel 261, which can be of rubber, and which is rotatably mounted between the forwardly extending legs of a U-shaped bracket 263 which is firmly secured to the edge of plate 38 as by screws 265. Wheel 261 is mounted within the bracket by a headed pin 266 extending through bores in the bracket legs, with flat washers 267 on either side of the wheel and with a cylindrical spacer 268 positioned between the upper washer and the upper bracket leg. To secure headed pin 266, a cotter pin 269 extends through pin 266 beneath the bottom of the bracket. Wheel 261 extends through an opening 270 in the side of cylinder 36 to permit its engagement with ramp 223, but to space it from rack 208.

A link rod 271, which can made of rigid metal, is offset as seen in FIG. 7, and has a vertical end 273 which extends within a conforming bore in wheel 261 so that the wheel bore grips ends 273 to resist its vertical movement but allows rotational movement therein. From the wheel, link 71 extends through an opening 272 in plate 38 and has a second vertically extending end which fits within the rolled tab 258 so as to be rotatable therein, and a rubber dust cover sheath 274 extends around the link on the exterior of end plate 38.

The circumference of the wheel 261, the length of the flat portion of ramp 223, and the length of link 271 and the positioning of its ends on the wheel 261 and clamp 255 are such that when the ramp 223 is moved from the position shown in phantom lines as 223' in FIG. 6, to the position shown in solid lines the flat portion of the ramp frictionally engages wheel 261 to rotate the wheel counterclockwise so that link 271 moves from the position shown in phantom lines in FIG. 6 as 271' to its position in solid lines in FIG. 6 to thus rotate valve section 244 by moving the handle to the position shown in FIG. 6 in phantom lines as 246' to its position in solid lines. Thus by forward movement of rack 208, liquid flow from outlet 55 is opened to catheter 251 through the counter-clockwise rotation of wheel 261.

The control unit 32 comprises a box housing 276 which has an electrical cord 278 with a plug which can be connected in a standard socket to supply A.C. electricity to the unit 32. Extending from box 276 is another electrical cord 280, shown broken in FIG. 1, which is electrically connected with box 276 to electricity supplied by cord 278, and which divides into two separate branches 282 and 284, each of which comprises two smaller electrical cords having conducting wires. Branch 282 is electrically connected to motor 83 as is well known in the art so that current can be supplied to power the motor, while branch 284 has its wires electrically connected to solenoid 90 so that lock rod 95 can operate by electrical activation of the solenoid core.

Electrical wires extending from the top of the box 276 merge into a third cord 286 that extends into electrical connection with motor 188 to allow the motor shaft to be rotated in both directions, and to operate the internal switch that reverses counterclockwise rotation of shaft 196.

Mounted on the top of box 276 are three switches, which can be standard rocker-arm switches that can be placed in a selected position and held in that position by the switch structure. Switch 287 is a two-position switch that can be placed in either an "on" or an "off" position. When switch 287 is "on", the electrical circuitry within box 276 supplies electricity to motor 83 through cord branch 282, so that the motor rotates shaft 88 and mount assembly 24 counterclockwise (from the rearend view of FIG. 3). When switch 287 is in the "off" position, the motor is not driven, and the shaft 88 and mount assembly 24 are likewise not driven.

Switch 289 also is a two position switch with an "on" and an "off" position. Switch 289 is wired within box 276 to supply electrically to cord branch 284. With switch 289 in the "on" position, the solenoid is energized so that the solenoid core is thrust forward moving solenoid lock rod 95 also forward toward the disk 119. In the "off" position, the solenoid core is electrically deenergized so there is no forward thrust on the solenoid core, and the spring 100 urges the lock rod 95 away from the disk toward the solenoid.

Switch 292 is a three-position switch having "forward", "reverse", and "off" positions. Switch 292 is electrically connected within box 276 so that when placed in the "forward" position, motor 188 is energized through cord 286 to rotate shaft 196 and gear 200 counterclockwise (as viewed looking at FIG. 5) to drive gear rack 208 forward thereby moving flange 228 forward. With switch 292 in the "reverse" position shaft 196 and gear 200 are rotated clockwise to drive rack 208 and flange 228 rearwardly. In the "off" position, the motor 188 is not energized and shaft 196, gear 200 and rack 208 are not driven.

OPERATION

The dispenser can be used in a fixed position, such as the emergency room or intensive care room at a hospital, or can be carried to a patient who is in an emergency condition elsewhere, such as at a worksite where an emergency has occured. The light weight of the dispenser allows it to be used easily by a single operator.

For purposes of demonstration switches 287, 289 and 292 are all initially in the "off" position and held in the "off" position by their switch structure. Consequently, initially the motor 83 is "off" and the mount assembly 24 stationary; and solenoid 90 is inactivated and the solenoid lock rod 95 is urged into disengagement from the lock bores of disc 119 by spring 100. Motor 188 is likewise initially "off" and rack 208 stationary with its rear end positioned at 208' as shown in phantom lines in FIG. 1, so that the compression flange is positioned at 228' as shown in phantom lines in FIG. 1, abutting rear most rack mounting bracket 210.

Initially, the springs 182 and 184 urge the syringe flanges 150 and 153 and their bodies, rearwardly so that body 146 has the position shown in solid lines in FIG. 1, and the other body is positioned at 148' as shown in phantom lines in FIG. 4. Initially the plungers 164 and 165 are in the rearwardly extended position, shown in FIG. 1 as solid lines for plunger 164, and in phantom lines in FIGS. 1 and 4 as 165' for the other plunger. In the rearmost extended positions each syringe contains its maximum liquid capacity which can be discharged through compression of the plungers. With the syringe bodies 146 and 148 in their rearmost positions, the syringe needles 155 and 157, and their end caps 159 and 161 are positioned rearward from end plate 38 so that they will not engage the inner puncture tube section 62 when the syringe assemblies are rotated by shaft 104.

The puncture tube 58, outlet tube 55, and stop cock tube 237 are also initially filled with dextrose. This can be done prior to filling catheter 251 with dextrose by hand-rotating the wheel so that the link 271 turns handle 246 to point toward catheter 251. With valve 250v in non-crimping position, dextrose can flow by gravity from bag 250 to fill tubes 55, 58 and 237. The stop cock assembly 30 is initially in the position shown in FIG. 6 in phantom lines, with the wheel 261 in a position such that the link 271' holds the stop cock handle 246' pointing toward the outlet tube 55. With the handle in that position with valve 250v in non-crimping position, dextrose flows from bag 250 by force by gravity through catheter 249 and into catheter 251 to fill it up to the end of needle 252. After catheter 251 has been filled, valve 250v can be operated to crimp catheter 251 to block further dextrose flow through catheters 249 and 251.

After these tubes and catheters are so filled, the needle 252 can then be inserted into the appropriate vein of the human body so that the selected liquid drug can flow through it into the body.

With the dispenser in this initial position, the dispenser can be operated by an individual to supply liquid from either of the plurality of syringes provided. This is accomplished by using the hand to place switch 287 in the "on" position to thereby cause motor 83 to rotate shaft 104 and mount assembly 24. When the assembly 24 begins rotating the operator can move switch 289 into the "on" position to activate the solenoid to drive lock rod 95 towards the selected disc lock bore 123 or 125 depending upon from which syringe it is desired to dispense liquid. For purposes of demonstration it is desired to dispense epinephrine to the patient, so syringe 143 is selected. The operator can turn switch 289 "on" to obtain locking of rod 95 in bore 123 by activating the switch after bore 125 has rotated past alignment with lock rod 95. After rotation bore 125 past alignment with rod 95, activation of switch 289 to the "on" position will thrust rod 95 forward towards the disc 119. If the rod is thrust forward prior to the rotation of bore 123 in to alignment with rod 95, the end of the rod will rest against the flat rear surface of disc 119 and slide upon it until alignment with bore 123 and then will be urged into bore 123 upon alignment by the solenoid thrust, as shown in FIG. 2. After its insertion in bore 123, rod 95 acts with end plate 40 as well as its mounting to the solenoid to lock disc 119 and mounting assembly 24.

With rod 95 inserted in lock bore 123, as shown in FIGS. 1, 2 and 3, syringe 143 and its needle 157 are in axial alignment with puncture tube 58 and its diaphragm 60 as previously discussed (FIG. 4), so that cap 161 occupies the position shown in phantom lines at 161' and the compression flange, at position 228' is directly axially behind the end of the plunger at 165'. With syringe 143 so positioned, syringe 141 is in the FIG. 1 position so that it will not interfere with flange 228 when flange 228 moves forwardly or rearwardly.

With the syringe 143 axially aligned with diaphragm tube 58, switch 292 can now be moved by the operator to the "forward" position so that motor 188 rotates gear 200 as aforesaid to drive rack 208 and flange 228 forward so that the flange is moved to the position shown in phantom lines at 228" in FIGS. 1 and 4. In this position the resilient pad 231 of the flange engages the rear end of the plunger at 165'. As flange 228 is moved forward from position 228" the syringe 143, being filled with liquid and having its needle 157 blocked by cap 161, is likewise moved forward because the liquid epinephrine cannot be compressed within the syringe and resists movement of the plunger 165 into the syringe body 148.

With the liquid epinephrine acting to resist movement of the plunger into the body 148, the plunger and body are moved from positions 165' and 148' to the positions shown in solid lines in FIGS. 1 and 4 with the front of the syringe body 148 flush against the front inner end of bore 166 of sleeve 139 during which the cap is moved forward from 161' until it engages the diaphragm 60. Diaphragm 60 flexes inward slightly as cap 161 moves into it, and resists forward movement of the cap so that needle 157 pierces the cap and diaphragm. It is noted as seen in FIG. 4 that the cap 161 has a diameter of greater thickness than the interior of tube section 64 so that should for any reason diaphragm 60 tear or otherwise fail, the cap 161 will be resisted by the end of tube section 64, and a seal maintained by cap 161 about section 64.

When needle 157 punctures its cap 161 and the diaphragm 60 there is no longer any blockage of flow through needle 157 and the compressive force exerted through flange 228 in the position shown in solid lines in FIG. 4, begins to compress the plunger 165 into the syringe body 148 to begin the discharging of the liquid within the syringe through needle 157 and into the puncture tube 58 and outlet tube 55. The needle 157, plunger 165 and syringe body 148 occupy the positions at this point shown in solid lines in FIGS. 1 and 4.

At this point in the discussion of the operation, attention is directed to the operation of the stop cock assembly 30 which is operated simultaneously with the forward movement of the syringe 143. As rack 208 and compression flange 228 are driven forward by motor 188, ramp 223 is also moved forward to engage wheel 261 and rotate it as previously described so that link 271 rotates stop cock handle 246 from the position 246' of FIG. 6 to the position shown for the handle in solid lines in FIG. 6.

When this positioning occurs, flow from the dextrose bag through line 249 to catheter tube 51 is blocked and liquid communication is established from outlet tube 55 to catheter 251 and needle 252.

Therefore, when the needle 157 has moved to its position puncturing diaphragm 60 as shown in FIG. 4, liquid flow has been established from puncture tube 58 and outlet tube 55 to needle 252. So as the plunger 165 continues to be driven forward by flange 228, the plunger compresses the liquid through syringe needle 157 into diaphragm tube 58 and thus through compressive fluid flow moves the dextrose previously supplied to line 251 through needle 252 into the body of the patient. The flange 228 continues to drive plunger 165 forward until the drug within the syringe 143 is fully discharged. Upon complete compression of plunger 165 the dextrose which was initially present in the catheter 251 and stop cock outlet tube 239, and the dextrose initially in the tubes 55, 58 and 237, has been injected into the patient. The volume of epinephrine injected depends on the initial volume of dextrose in tubes 55, 58, 237 and 239. This volume is of course dependent upon the length as well as the internal diameter of discharge catheter 251, which can be two millimeters. In the embodiment shown, this total volume is 3 milliliters, and therefore seven milliliters of epinephrine contained with the ten milliliter syringe 143 is injected into the patient. The remaining three milliliters of epinephrine is within tubes 55, 58 and 237, 239 and 251. The patient has thus been supplied the amount of epinephrine desired.

When the plunger 165 is completely compressed to discharge the ten milliliters of epinephrine contained within it, the end of the plunger is flush with the end of cap 172, and the rear end of the plunger has engaged the rear end of washer 149, so that the liquid in the plunger has been discharged through the washer orifice. The forward movement of flange 228 is resisted by engagement of resilient pad 231 against the rear of cap 172, which resists forward movement by virtue of its attachment to sleeve 139 and the sleeve engagement in wing 124. The resulting force against flange 228 is transferred through rack 208 and pinion 200 to shaft 196 and motor 188. The strong resistant force is of sufficient amount to activate the internal reversal switch of motor 188 to automatically reverse rotation of pinion 200 so that the pinion drives rack 208 and flange 228 rearward. The operator can, of course, operate switch 292 to the "reverse" position after the pad 231 engages cap 176 to accomplish this reverse movement of flange 228 but the automatic reversal allows for greater convenience. The resistant force exerted against flange 228 in moving the plunger through its discharge stroke is insufficient to activate the reversal switch.

Flange 228 continues to move rearward upon automatic reversal until it engages against bracket 210, and when this occurs the operator can move switch 292 "off" to stop movement of rack 208 and flange 228. As flange 228 moves rearward after complete compression, spring 184 urges syringe flanges 153 rearward until they engage the inner ends of slots 176, so that the syringe body 148 returns to its initial position. With the compression flange at position 228' against rear bracket 210, the needle 157 and cap 161 have moved rearward by virtue of the rearward urging of spring 184 on the syringe, so that needle 157 no longer penetrates diaphragm 60 and therefore will not engage puncture tube 58 when syringe 143 rotated.

Occurring simultaneously with the rearward movement of rack 208, ramp 223 is moved rearward to again engage wheel 261 and rotate it clockwise so that link 271 moves stop cock handle 246 back to its position shown as 246' in FIG. 6, so that flow from tube 55 to catheter 251 is blocked. Therefore, if desired, needle 252 can now be removed from the patient, and catheter 251 and needle 252 can be rinsed with a solution of dextrose from bag 250 by placing valve 250v in open position to allow flow through catheter 249, so that catheter 251 and needle 252 can be again filled with dextrose.

When the flange is at its rearmost position 228', syringe 141 can be rotated to discharging positions to supply the patient forty-seven milliliters of calcium chloride. This is done by turning solenoid switch 289 "off" so that spring 100 urges lock rod 95 out of engagement from lock bore 123. Switch 287 is still in the "on" position (unless the operator selected to turn it "off" after engagement with lock rod 95 and bore 123,) so that disc 119 is rotated. When this rotation begins, switch 289 can be turned "on" so that lock rod 95 is again thrust forward toward disc 119. Rod 95, if activated before bore 125 becomes aligned with it, will slide on the rear of disc 119 as previously discussed until such alignment occurs, and then will enter lock bore 125 to lock disc 119 and thereby lock syringe 141 in alignment with tube 58. After such alignment occurs, switch 292 can be moved to the "forward" position so that flange 228 is operated in the same manner described for syringe 143 to engage plunger 164 and drive syringe 141 forward to cause cap 150 to engage the diaphragm 60, so that needle 155 pierces cap 159 and diaphragm 60, and compression of plunger 164 compresses the calcium chloride through needle 155 into the puncture tube 58 and outlet tube 55. Simultaneously with this movement, wheel 261 is driven by ramp 223 to move handle 246 to open tube 55 to catheter 251 before needle 155 pierces diaphragm 60.

Therefore, when flange 228 strikes the rear of cap 169, plunger 164 has been fully compressed, and forty-seven milliliters of calcium chloride is compressed through catheter 251 and needle 252 into the patient's body. The calcium chloride can be supplied to the patient without rinsing tube 251 and tube 239 with dextrose, in which case compression of the calcium chloride through tubes 58, 55, and 237, 239 and 251 also drives the three milliliters of epinephrine into the patient through needle 252, if a total dosage of ten milliliters of epinephrine is desired. If tubes 239 and 251 have been rinsed, then the patient is supplied the amount of dextrose in tubes 239 and 251, plus the epinephrine remaining in tubes 55, 58 and 237.

After flange 228 is resisted by cap 169, motor 188 is reversed automatically as previously described for syringe 143 operation and flange 228 can be returned to abutment against rear bracket 210, or if desired the operator can move switch 292 to "reverse" to move flange 228 backward against rear bracket 210. As the compression flange 228 moves rearwardly, spring 182 urges syringes flange 150 against the ends of slots 174 so that syringe body 146 is returned to its initial position, and needle 155 is withdrawn away from diaphragm 60 so that assembly 24 can be rotated without interference when flange 228 is returned to its rearmost position.

Thus the single operator has dispensed epinephrine and calcium chloride to the patient through the automatic dispenser with a minimum of manual effort, and without the assistance of another operator. Although for demonstration purpose, syringe 143 was selected first, syringe 141 can also be selected first, and the operator can dispense either one of the drugs separately, without dispensing the other, or can dispense both drugs. The dispenser can be operated to move the syringe plunger to discharge and use their full capacity through the syringe needle by use of measuring assembly 29. For demonstration purposes, syringe 143 operation is selected to demonstrate this.

The operator can dispense less than 7 milliliters of epinphrine to the patient and since syringe 143 has been selected, scale 134a is used in conjunction with stem 233.

As previously described, flange 228 is moved forward from its initial position by moving switch 292 to "forward" so that the flange moved from position 228' to position 228' to engagement with the rear of the plunger at 165' and the flange drives syringe 143 forward to the positions shown in solid lines for flange 228 and syringe 143 in FIGS. 1 and 4. The flange and rack 208 move forward from this position and drive plunger 165 into the syringe body 148, and when plunger 165 has been driven to the position so that the plunger numbered lines shown a reading of three milliliters discharged, stem hairline H is aligned with the scale 134a line for zero milliliters discharged. At this point three millimiters of epinephrine have been discharged through needle 157, and tubes 58, 55, 237, 239 and 251 and needle 252 have had the dextrose initially contained within them discharged into the patient, and are now filled with epinephrine. As rack 208 and flange 228 move forward from this position, epinephrine is discharged through needle 252. The volume discharged can be read by observing the alignment of line H with scale 234a. If it is, for example, desired to dispense four milliliters of epinephrine through needle 252 into the patient, the operator allows rack 208 to move forward until he sees the four milliliter line on scale 134a aligned with stem line H. When this alignment occurs switch 292 can be moved by the operator to the "off" position so that rack 208 and flange 228 movement is stopped with scale 134a reading four milliliters. Switch 292 can then be quickly moved to "reverse" to move flange 228 rearward away from the syringe 143 and back against rear bracket 210. It is noted here that the strength of spring 184 is sufficient enough to urge syringe body 148 rearward when no force is exerted against the end of plunger 165, but not strong enough to move body 148 rearward when plunger 228 is stopped before full compression of the plunger, or strong enough to permit relative movement of body 148 toward plunger 165 when the flange is moved by motor 188 in reverse. The same is true for the strength of spring 182 against body 146. As flange 228 is moved rearward, spring 184 urges syringe body 148 rearward as previously described so that the syringe flanges 153 move against the ends of slots 176. Four milliliters of epinephrine has thus been discharged through needle 252, three milliliters of epinephrine remains in tubes 58, 55, 237, 239, 251 and needle 252, and three milliliters of epinephrine remains in syringe 143.

In like manner when syringe 141 is in discharge position plunger 164 of syringe 141 can be compressed to discharge less than its fifty milliliter capacity through needle 155. Flange 228 is moved from its initial position at 228' to engagement against the rear of plunger 164 to drive syringe 141 forward until needle 155 pierces diaphragm 60 as previously described. After this puncturing occurs, flange 228 continues to move forward to drive plunger 164 into syringe body 146 to discharge calcium chloride through needle 155. When the plunger 164 has moved to the position such that the plunger numbered lines show three milliliters discharged, the stem hairline H is aligned with the line for zero milliliters discharged on the other scale 134b. 208. The three milliliters discharged from syringe 141 at this point is now in tubes 58, 55, 237, 239 and 251 as well as needle 252. The dextrose initially in these tubes, assuming this operation for dispensing from syringe 141 occurs with tubes 55, 58, 237, 239 and 251, and needle 252 filled with dextrose, has been dispensed into the patient's body.

From this position, with stem hairline H aligned with the zero milliliter line on scale 134b, the switch 292 can be maintained in the "forward" position until the desired amount of calcium chloride is discharged through needle 252 into the patient, as indicated by alignment of the stem hairline H with the scale lines on scale 134b. For example, if it is desired to discharge twenty milliliters through needle 252, the operator turns switch 292 "off" when rack 208 has moved forward so t'at scale 134b reads twenty milliliters. When this is done, twenty milliliters of calcium chloride has been discharged through needle 252 into the patient, three milliliters of calcium chloride remain in tubes 58, 55, 237, 239 and 251 and needle 252, and twenty-seven milliliters of calcium chloride remain in syringe 141. The operator can then position switch 292 to "reverse" so that the flange 228 is moved rearward against bracket 210 and springs 182 urge flanges 150 of syringe body 146 rearward against slots 174, thus withdrawing needle 155 from diaphragm 60.

There has thus been shown a new and unique drug dispenser which can be operated by a single person to dispense a selected amount of drug from a plurality of movably mounted drug containers that can be utilized in a stationary zone or can be portably carried to an emergency site and operated at that site. If electricity is not available at an emergency site, electrical current can be supplied through a battery source that can be carried with the dispenser. The plexiglas frame provided, besides being of light weight, permits the operator to view operation of the assembly, and also prevents dust and contents from entry within the cylinder. All openings into the frame can be made of such size to show a minimum of opening clearance space between the walls of the openings and any extension that pass through them.

The lid 44 can be unfastened and lifted by handle 48 to permit the operator to insert his hands inside the container to make any adjustments on repairs. Although the end plates 38 and 40 have been described as being glued to cylinder 36, each can be detachably engaged to the cylinder by screws or the like to permit interchanging of the mounting assembly and other parts.

Control unit 32, shown detached from the frame in the drawings, can be mounted securely to the frame. Bag 250 can also be mounted on the top of the frame for gravity feed, and of course another shape and type of container for the dextrose, such as a transparent plexiglass box can be used and mounted on the frame. Also lock disc 119 can have markings, such as color markings, on the edge and front of the disc to indicate the position of the lock bores.

Although the operation has been described as pertaining to a plurality two particular drug containers, a greater number of containers, such as the syringes utilized, can be mounted on the rotatable assembly, and the lock bores can be provided in the disk 119 in such manner that locking of pin 95 in the lock bores will align any one of the plurality of syringes provided with the puncture tube 58. Although a rotatable drug mounting assembly has been illustrated, it is understood that the drugs can be mounted for linear movement, although the arrangement for rotatable movement provides for greater compactness of the dispenser.

Various changes and modifications may be made within this invention as will be readily apparent to those skilled in the art. Such changes and modifications are within the scope and teaching of this invention as defined by the claims appended hereto.

What is claimed is:

1. A fluid drug dispenser for dispensing fluid from a plurality of fluid containers comprising:
    (a) a frame;

(b) a mounting assembly movably supported relative to the frame for mounting the plurality of containers;

(c) a fluid conduit associated with the frame for receiving fluid from a selected container;

(d) means for moving the mounting assembly to position a selected container in a position for discharging fluid from a container to the conduit and (e) means for forcing liquid from the selected container into the conduit when the selected container is in the discharging position, said forcing means operable to act upon the selected container to discharge fluid with the mounting assembly and other containers remaining in fixed position relative to the frame, said forcing means comprising a forcing member mounted relative to the frame and movable relative to the frame to engage the selected container; and (f) means for passage to surround the liquid as the liquid moves from the container into the conduit.

2. The structure of claim 1 wherein the forcing member comprises an elongated part movably secured to the frame.

3. The structure of claim 1 wherein the forcing means comprises means to move the forcing member in a first direction and means to automatically reverse the movement of the forcing member in a second direction when the forcing member travels a predetermined distance in the first direction.

4. The structure of claim 1 further comprising control means to control the operation of said means for moving the mounting assembly and said forcing means.

5. The structure of claim 1 further comprising valve means associated with the conduit for obstructing fluid flow through the conduit in a first position and for opening fluid flow through the conduit in a second position, and further comprising means associated with the forcing means to move the valve from one valve position to the other valve position by operation of the forcing means.

6. The structure of claim 5 wherein the valve positioning means comprises linkage operable by the forcing means to position the valve.

7. The structure of claim 5 wherein the valve positioning means comprises a rotatable member positioned to engage the forcing means during operation of the forcing means, and a link extending from the rotatable member to association with the valve to position the valve upon rotation of the rotatable member.

8. The structure of claim 7 wherein the valve comprises a valve having an extension secured to a movable valve section for placing the valve in said first and second positions and wherein said link is secured to the valve extension.

9. The structure of claim 1 further comprising means to lock the mounting assembly relative to the conduit when the selected container is placed in discharging position.

10. The structure of claim 9 wherein the mounting assembly comprises a plate, and wherein said locking means comprises a member with means for engaging said plate to hold the plate in a selected position.

11. The structure of claim 10 wherein said locking means comprises a pin and a solenoid to move the pin to engage the plate.

12. The structure of claim 11 wherein said plate has an indentation to receive the pin to engage the plate.

13. The structure of claim 9 further comprising control means to control the operation of said means for moving the mounting assembly, said forcing means, and said locking means.

14. The structure of claim 1 further comprising means for locking the mounting assembly relative to the conduit when the selected container is placed in discharging position.

15. The structure of claim 14 wherein said locking means comprises means for engaging the mounting assembly.

16. The structure of claim 15 wherein said mounting assembly comprises a plate, and wherein said locking means comprises a member engageable with the plate to hold the mounting assembly in locked position.

17. The structure of claim 16 wherein said locking means comprises a pin and a solenoid to move the pin to engage the plate.

18. The structure of claim 14 further comprising control means to control the operation of said means to move the mounting assembly and said locking means.

19. The structure of claim 1 further comprising: measuring means associated with the forcing means to measure the volume of fluid flow through the conduit.

20. The structure of claim 19 wherein said forcing means includes an elongated member and said measuring means comprises a position indicator to indicate the position of the elongated member relative to the mounting assembly.

21. The structure of claim 20 wherein said measuring means comprises a counter scale associated with the frame so that the position of said forcing member relative to said scale can be calculated.

22. The structure of claim 1 wherein said mounting assembly is rotatably supported by the frame.

23. The structure of claim 1 further comprising biasing means associated with the mounting assembly for urging a container away from the conduit.

24. The structure of claim 1 further comprising a diaphragm positioned to obstruct the conduit and further comprising means to seal the container so that the container can be moved relative to the mounting assembly so that the means to seal engages the diaphragm.

25. The structure of claim 1 further comprising containers of the type having a needle outlet, a diaphragm associated with the conduit; and a sealing member positioned on a container needle to block flow through the needle and aligned with the diaphragm when said container is in the discharging position so that the needle can be moved towards the diaphragm so that the sealing member engages the diaphragm and upon such engagement be further moved to puncture the sealing member and the diaphragm to allow flow through the needle past the diaphragm.

26. The structure of claim 1 wherein the frame is transparent.

27. The structure of claim 1 further comprising control means to control operation of said means for moving the mounting assembly.

28. A fluid drug dispenser for dispensing fluid from a plurality of drug containers comprising:

(a) a frame;

(b) a mounting assembly movably mounted with the frame for mounting the plurality of fluid containers;

(c) a fluid conduit positioned in fixed position relative to the frame for receiving fluid from a selected container;

(d) means for moving the mounting assembly to place a container selected from the plurality of containers in position for discharging fluid from the container to the conduit;

(e) means to lock the mounting assembly to lock the selected container in discharging position;

(f) valve means associated with the conduit to block fluid flow through the conduit when said valve means is in a first position and to allow fluid flow through said conduit when said valve means is in a second position;

(g) means to force fluid from the selected container when the selected container is in the discharging position;

(h) valve positioning means operable by said forcing means to move said valve means fron one position to the other position.

29. The structure of claim 28 further comprising measuring means associated with the forcing means for indicating the amount of fluid discharged through a selected point of the conduit by the location of the forcing means.

30. The structure of claim 29 wherein said forcing means comprises a member movable relative to the frame and said measuring means comprises a position indicator to indicate the position of the forcing member.

31. The structure of claim 28 further comprising urging means associated with the mounting assembly to urge a container away from the conduit.

32. The structure of claim 28 further comprising means to seal the container, and blocking means associated with the conduit, with the sealing means and blocking means being aligned with one another for engagement by the forcing means when a selected container is in discharging position.

33. The structure of claim 28 wherein said mounting assembly is rotatably mounted within the frame, wherein said locking means comprises a member engageable with the mounting assembly, wherein said forcing means comprises a member movable relative to the frame, and said valve positioning means comprises linkage engaging the forcing member to the valve means.

34. The structure of claim 28 further comprising control means to control operation of the means for moving the mounting assembly, the forcing means, and the locking means.

35. A drug dispenser for dispensing fluids from a plurality of drug containers comprising:
(a) a mounting assembly rotatably mounted with the frame for mounting the plurality of fluid containers;
(b) a fluid conduit positioned in fixed relationship to the frame for receiving fluid from a selected container;
(c) means associated with the mounting means for urging a container away from the conduit;
(d) means for moving the mounting assembly to place a container selected from the plurality of containers in position for discharging fluid from the container to the conduit;
(e) means to lock the mounting assembly to lock the selected container in discharging position;
(f) valve means associated with the conduit for obstructing fluid flow through the conduit in a first position and for opening fluid flow through the conduit in a second position;
(g) means to overcome said urging means to force fluid from the selected container when the selected container is in the discharging position;
(h) valve positioning means operable by activation of said forcing means to move said valve means from one position to the other position.

36. The structure of claim 35 further comprising control means to control the operation of said means for moving the mounting assembly, said forcing means, and said locking means.

37. The structure of claim 35 further comprising measuring means associated with said forcing means to indicate the volume of flow through the conduit.

38. The structure of claim 35 further comprising means to seal said conduit and means to break said seal to allow entry of fluid from a selected container into the conduit.

39. A fluid drug dispenser for dispensing fluid from a plurality of fluid containers comprising:
(a) a frame;
(b) a mounting assembly movably supported relative to the frame for mounting the plurality of containers;
(c) a fluid conduit associated with the frame for receiving fluid from a selected container;
(d) means for moving the mounting assembly to position a selected container in a position for discharging fluid from the container to the conduit;
(e) means for forcing liquid from the selected container into the conduit when the selected container is in the discharging position; and,
(f) valve means associated with the conduit for obstructing fluid flow through the conduit in a first position and for opening fluid flow through the conduit in a second position, and further comprising means associated with the forcing means to move the valve from one valve position to the other valve position by operation of the forcing means.

40. The structure of claim 39, wherein the valve positioning means comprises linkage operable by the forcing means to position the valve.

41. The structure of claim 39 wherein the valve positioning means comprises a rotatable member positioned to engage the forcing means during operation of the forcing means, and a link extending from the rotatable member to association with the valve to position the valve upon rotation of the rotatable member.

42. The structure of claim 1 wherein the means for passage is associated with the selected container.

43. The structure of claim 1 wherein the means for passage is associated with the selected container, and wherein the means for passage is provided by moving the container towards the conduit so that fluid can flow into the conduit.

44. The structure of claim 43 wherein the passage means includes a tubular extension from the container which can be moved to allow flow of fluid into the conduit.

45. A fluid drug dispenser for dispensing fluid from a plurality of fluid containers comprising:
(a) a frame;
(b) a mounting assembly movably supported relative to the frame for mounting the plurality of containers;
(c) a fluid conduit associated with the frame for receiving fluid from a selected container;

(d) means for moving the mounting assembly to position a selected container in a position for discharging fluid from the container to the conduit, and (e) means for forcing liquid from the selected container into the conduit when the selected container is in the discharging position, said forcing means operable to act upon the selected container to discharge fluid with the mounting assembly and other containers remaining in fixed position relative to the frame;

(f) means for passage to surround the liquid as the liquid moves from the container into the conduit, said passage means provided by moving the selected container towards the conduit; and (g) valve means associated with the conduit for obstructing fluid flow through the conduit in a first position and for opening fluid flow through the conduit in a second position, and further comprising means associated with the forcing means to move the valve from one valve position to the other valve position by operation of the forcing means.

46. A fluid drug dispenser for dispensing fluid from a plurality of fluid containers comprising:

(a) a frame;

(b) a mounting assembly movably supported relative to the frame for mounting the plurality of containers;

(c) a fluid conduit associated with the frame for receiving fluid from a selected container;

(d) means for moving the mounting assembly to position a selected container in a position for discharging fluid from the container to the conduit with a cross section of the selected container moving in only a single plane during movement of the mounting assembly to the discharging position; and (e) means for forcing fluid from the selected container into the conduit when the selected container is in the discharging position said forcing means comprising a forcing member mounted relative to the frame and movable relative to the frame to force fluid from the selected container.

47. A fluid drug dispenser for dispensing fluid from a plurality of fluid containers comprising:

(a) a frame;

(b) a mounting assembly movably supported relative to the frame for mounting the plurality of containers;

(c) a fluid conduit associated with the frame for receiving fluid from a selected container;

(d) means for moving the mounting assembly in the direction of only two geometrical coordinates relative to the frame to position a selected container in a position for discharging fluid from the container to the conduit; and (e) means for forcing fluid from the selected container into the conduit when the selected container is in the discharging position, said forcing means comprising a forcing member mounted relative to the frame and movable relative to the frame to force fluid from the selected container.

48. The structure of claim 47 wherein the means for moving the mounting assembly rotates the mounting assembly relative to the frame.

* * * * *